(12) United States Patent
Bessri et al.

(10) Patent No.: US 9,316,621 B2
(45) Date of Patent: Apr. 19, 2016

(54) INSTALLATION FOR NON-DESTRUCTIVE TESTING, BY IMMERSION ULTRASOUNDS, OF WORKPIECES

(75) Inventors: Kamal Bessri, Soisy sur Seine (FR);
Pascal Bardouillet, Saint Remy (FR);
Louis Bettega, Boucheporn (FR);
Francois Jean-Pierre Mirville, Hericy (FR)

(73) Assignee: SNECMA, Paris (FR)

(*) Notice: Subject to any disclaimer, the term of this patent is extended or adjusted under 35 U.S.C. 154(b) by 284 days.

(21) Appl. No.: 14/004,909

(22) PCT Filed: Mar. 15, 2012

(86) PCT No.: PCT/FR2012/050551
§ 371 (c)(1),
(2), (4) Date: Sep. 13, 2013

(87) PCT Pub. No.: WO2012/123687
PCT Pub. Date: Sep. 20, 2012

(65) Prior Publication Data
US 2014/0000372 A1   Jan. 2, 2014

(30) Foreign Application Priority Data
Mar. 16, 2011  (FR) ...................................... 11 52150

(51) Int. Cl.
*G01N 29/28*  (2006.01)
*G01N 29/24*  (2006.01)
(Continued)

(52) U.S. Cl.
CPC ................ *G01N 29/28* (2013.01); *G01N 29/24* (2013.01); *G01N 29/26* (2013.01); *G01N 29/265* (2013.01); *G01N 2291/048* (2013.01); *G01N 2291/102* (2013.01); *G01N 2291/2693* (2013.01)

(58) Field of Classification Search
CPC ....... G01N 29/28; G01N 29/24; G01N 29/26; G01N 29/265; G01N 29/07; G01N 29/223
USPC .......................... 73/644, 649, 660, 661, 632
See application file for complete search history.

(56) References Cited

U.S. PATENT DOCUMENTS 4,127,033 A    11/1978  Warren et al.
4,241,430 A  * 12/1980  Kayem et al. ................. 367/115
(Continued)

FOREIGN PATENT DOCUMENTS

DE          41 13 519      10/1992
EP          1 788 386       5/2007
WO       2007 008620       1/2007

OTHER PUBLICATIONS

International Search Report Issued May 31, 2012 in PCT/FR12/050551 Filed Mar. 15, 2012.

*Primary Examiner* — Helen Kwok
(74) *Attorney, Agent, or Firm* — Oblon, McClelland, Maier & Neustadt, L.L.P.

(57) ABSTRACT

To test transverse flanges terminating at a cylindrical wall of a workpiece, an installation includes a structure in a form of a U-shaped or C-shaped stirrup whose opposite branches carry respectively an ultrasound emitter transducer and receiver transducer, aligned with respect to one another, while leaving between them an internal space for relative passage of the flange to be tested, and whose base is mounted articulated at an extremity of a mobile control arm. The installation also includes an immersion canister including two parts assembled together by a closure mechanism, one of the parts exhibiting cutouts for engaging the transverse flange and for overlapping, with the other part, the flange up to the cylindrical wall of the workpiece.

9 Claims, 3 Drawing Sheets

(51) Int. Cl.
  *G01N 29/26* (2006.01)
  *G01N 29/265* (2006.01)

(56) References Cited

U.S. PATENT DOCUMENTS

| | | | |
|---|---|---|---|
| 4,483,343 A * | 11/1984 | Beyer et al. | 600/437 |
| 4,637,256 A * | 1/1987 | Sugiyama et al. | 73/633 |
| 4,881,177 A | 11/1989 | McClean et al. | |
| 4,917,096 A * | 4/1990 | Englehart et al. | 600/446 |
| 7,337,672 B2 * | 3/2008 | Blake et al. | 73/600 |
| 2004/0129081 A1 * | 7/2004 | Stauffer | 73/588 |
| 2006/0243051 A1 * | 11/2006 | Bui et al. | 73/618 |
| 2007/0113655 A1 | 5/2007 | Reed | |
| 2008/0276710 A1 * | 11/2008 | Pierson | 73/632 |
| 2009/0272190 A1 * | 11/2009 | Hofmann | 73/599 |
| 2009/0314089 A1 * | 12/2009 | Brignac et al. | 73/622 |
| 2010/0089164 A1 * | 4/2010 | Aoike et al. | 73/632 |

* cited by examiner

INSTALLATION FOR NON-DESTRUCTIVE TESTING, BY IMMERSION ULTRASOUNDS, OF WORKPIECES

BACKGROUND OF THE INVENTION

1. Field of the Invention

The present invention relates to an installation for the non destructive ultrasonic immersion testing of parts.

2. Description of the Related Art

In a preferential application of the invention, the installation is designed for testing tubular parts of turbomachines, such as fan casings of jet engines, it being understood that the invention could also be used for other types of part.

This type of part is known to be axisymmetric and to have manufacturing singularities such as regions having transverse end flanges for connecting to adjacent parts, connecting regions having variable inner and outer radii between the flange regions and the cylindrical wall of the tubular part, in which the air stream flows and which forms the principal region thereof, often having changes in thickness, holes, perforations or similar in the flange regions, etc. The casing is, moreover, made of a woven composite material consisting of a monolithic structure with three dimensional weaving of carbon fibers, of carbon fiber preforms and of an injected epoxy resin acting as a binder for the whole.

One example of such a tubular part to be tested is shown in FIG. 1, illustrating an outer casing 1 of a fan for a jet engine which has a longitudinal axis of symmetry X and is made of a high absorption composite material, which is why it is an ultrasonic transmission testing installation that is preferably chosen for a structural inspection of the material.

In particular, the casing 1 is defined by a cylindrical wall 2 (principal region) having variable thicknesses and delimiting the duct for air entering the fan, and by two transverse end flanges 3, 4 (flange regions) which terminate the wall 2 and which extend radially outward with respect to thereto. The transverse end flanges project from the cylindrical wall 2 via respective intermediate connecting regions 5 and 6, each having a small inner radius on the flange side and a large outer radius opposed thereto. Holes 7 are moreover created in the flanges, through which fastening members (not shown) can pass, to permit connection to other parts.

In addition, in order to test these composite tubular parts having transverse flanges, the size of which is, moreover, significant (the diameter can reach two meters for a coaxial length of approximately one meter), an ultrasonic immersion testing installation is used, such an installation being particularly well suited to detecting therein, in terms of searched-for defects, delamination or loss of cohesion of the plies of the woven fabric at their interface, microcracking around perforations and machined features, inclusions, foreign bodies, dry areas without resin or areas with excess resin, etc.

A prior art testing installation 9, using the ultrasonic immersion technique, is shown in part and schematically in FIG. 2 and comprises transducers for emitting and receiving ultrasound. The transducer 10 which emits an ultrasound beam is mounted on a support 11 located at the end of a robotic arm 12 and, in this example, is oriented toward the outer periphery of the casing 1 which defines the tubular part. The transducer 13 which receives the beam, and is aligned coaxially with the emitter transducer 10, is mounted on a support 14 located at the end of another robotic arm 15 and is then oriented toward the inner periphery of the casing 1. Thus, between the aligned transducers 10, 13, is the casing 1, of which the constituting wall, made of composite material, is then tested by a relative movement of the two synchronized robotic transducers with respect to the part 1.

Water jet nozzles 16, 17 are of course provided on the arms, coaxially with the transducers, and make it possible to facilitate the appropriate transmission or propagation of the beam of ultrasound waves by a continuous water jet in order to "couple" the transducers to the part, the latter being arranged in a container or a place specially conceived to that effect for recovering the liquid.

Although this installation gives good analysis results with respect to the ultrasound technique employed, it nonetheless presents drawbacks linked, in particular, to the geometry—having singularities—of the part.

Indeed, while such an installation tests the cylindrical wall effectively, with the transducers acting perfectly perpendicular thereto as in FIG. 2, it does not by contrast allow optimum accessibility to the regions having external transverse flanges 3, 4 and to the connecting regions 5, 6 of the fan casing 1, in particular the small radius connecting region of each of the flanges, on the side of the outer periphery of the casing.

This is due to the fact that the support 11 for the nozzle and for the transducer in question (the emitter in this example) is too bulky, with the result that, after having followed, perpendicular thereto, the outer periphery of the cylindrical wall 2, it cannot turn sufficiently in order to follow the region of curvature of the connector and the transverse flange in question. As shown by the chain line representation in FIG. 2, the support 11 for the nozzle 16 touches the cylindrical wall 2 as soon as the transducer 10, driven by the arm 12, starts to pivot in order to follow, perpendicular thereto, the regions in question 3 and 5, such that the positioning of the two transducers is incorrect and, as a consequence, the profile is not correctly followed and the testing is imperfect. Thus, some of the aforementioned defects might not be identified.

This problem does not arise for the support 14 for the nozzle 17 and for the other transducer 13, which is in no way encumbered by the transverse flange.

It should also be noted that synchronizing the two robotic arms, in order to keep the transducers in coaxial arrangement when following the flange regions and curved connectors, makes automating the installation more complex.

Furthermore, the testing itself of the tubular casing part, with its singularities, is relatively long since, after testing one transverse end flange, it is then necessary to test the opposite flange with, once again, the aforementioned problems.

Moreover, the installation makes it necessary to provide a container of considerable size in order to receive the fan casing and to recover the water sprayed by the nozzles.

BRIEF SUMMARY OF THE INVENTION

The present invention aims to provide a solution to these drawbacks and relates to an installation for ultrasonic immersion testing which, by its design, makes it possible to perfectly test singularities of tubular parts, such as regions having transverse end flanges and the connecting regions having inner and outer radii.

To that end, the installation for the ultrasonic immersion testing of a tubular part having a cylindrical wall terminated by transverse end flanges, of the type comprising controllable transducers for emitting and for receiving ultrasounds and which are designed to be arranged such that they are aligned respectively on either side of the flange to be tested, is noteworthy in that it comprises a structure in the form of a U shaped or C shaped stirrup, wherein the opposing branches bear respectively the emitter transducer and the receiver transducer aligned with respect to each other, creating between them a space through which the flange to be tested can pass, and wherein the base is mounted in an articulated manner at the end of a moveable control arm.

Thus, by virtue of the invention, accessibility to the flanges and to the connecting regions of the part is total, this being made possible by means of one and the same stirrup shaped (or clevis shaped) structure bearing the transducers in place of the two independent supports initially provided in the earlier installation. This structure makes it possible to reduce the size by virtue of the inherent U shape or C shape of the stirrup, to introduce the flange into the stirrup between the transducers attached to the branches thereof by following the profile in a suitable manner, and to access the radiused connecting regions by pivoting the structure while still keeping the transducers aligned perpendicular to the encountered profile of the curved connecting region of the casing. The testing of the material of the part and of its singularities is then optimal, without any contact between the part and the stirrup.

The entire periphery of the transverse flange, between which the branches of the stirrup engage in parallel, can be tested by virtue of a relative movement between the structure and the part, and the movement of the structure makes it possible to follow and test the radiused connecting regions as far as the principal transition region.

Moreover, a single robotic arm is then used in order to test the transverse flange in place of the two robotic arms of the earlier installation.

Finally, the simplicity of creating the structure in the form of a simple U shaped stirrup should be noted. Such a structure thus makes it possible to follow the profile of each transverse flange and of the associated radiused regions.

Advantageously, the emitter and receiver transducers are positioned at the ends of the opposing branches of the stirrup shaped structure, making it possible to optimize the depth and thus the internal space of the stirrup in order to receive the flange or other similar large singularity, and to move the stirrup without touching the flange.

Moreover, the emitter and receiver transducers are mounted such that they can be adjusted with respect to the respective opposing branches, making it possible to adapt their separation and focusing depending on the thickness of the flange to be tested.

According to another feature of the installation, the stirrup shaped structure bearing the transducers is arranged in an immersion container (or tub) which contains a liquid for coupling the transducers to one another and which is arranged over the flange to be tested. Thus, only partial immersion of the regions of the part that are to be tested, around the transducers, is required for the inspection and to ensure the coupling of the ultrasound waves between the transducers, without the need for an oversized tank big enough to hold the casing (the diameter of which can reach two meters) or a dedicated space therefor.

For example, the immersion container straddles the flange with sealing as far as the cylindrical wall and can be moved relative to the part in order to permit a full test of the periphery of the flange.

The immersion container is preferably immobile with respect to the tubular part which can be rotated about its longitudinal axis of symmetry, said immersion container having rolling members designed to engage with the transverse outer face of the flange, making it easier to rotate the part with respect to the container.

The immersion container can, in particular, comprise two portions which are joined together using a closing means, one of the portions having cutouts for engaging the transverse flange and for straddling, with the other portion, said flange as far as the cylindrical wall of the part, seals being provided between the joined together portions and the part.

In order to rotate the part with respect to the immobile immersion container, a controllable rotating plate can rotate the tubular part.

Advantageously, two structures in the form of stirrups having emitter transducers and receiver transducers and respective controllable arms are provided so as to be able to test, simultaneously, the two transverse end flanges of the tubular part. The two robotic arms of the earlier installation can thus be used simultaneously for testing the two end flanges and the connecting regions of the casing, thus reducing testing times. The two arms are also used to test the cylindrical wall or principal region of the casing in the same way as in the preceding installation.

BRIEF DESCRIPTION OF THE SEVERAL VIEWS OF THE DRAWINGS

The realization of the invention will be readily understood with reference to the figures of the appended drawing.

DETAILED DESCRIPTION OF THE INVENTION

Figure 1:
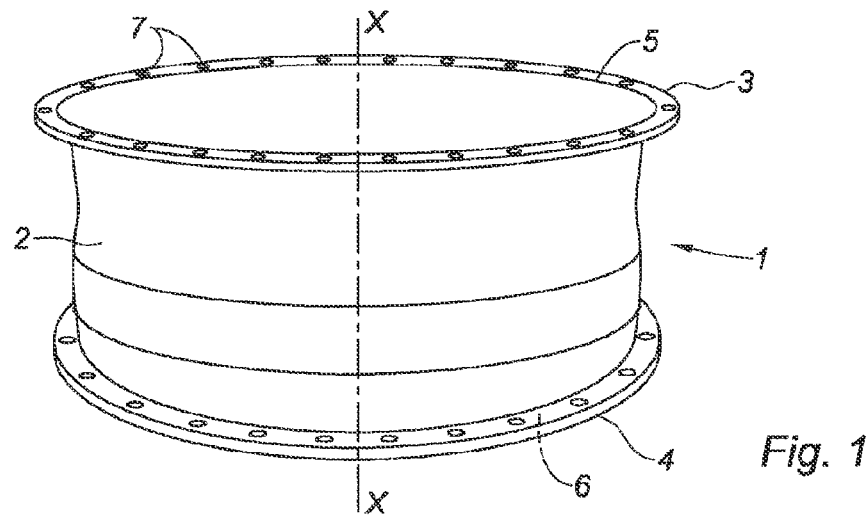
FIG. 1 shows, in perspective, an exemplary embodiment of an axisymmetric part to be tested by the installation according to the invention.

The axisymmetric part to be tested which is shown in FIG. 1 is, as stated previously, an outer casing 1 of a fan for a jet engine which has a longitudinal axis of symmetry X and is made of a high absorption composite material. An ultrasonic transmission testing installation is, because of this high absorption, to be chosen for a structural inspection, although such an installation would also be suitable for a metal. This casing will not be described in any more detail and the same reference numbers are assigned thereto.

The casing 1, having all of these flanges 3, 4, connecting regions 5, 6, changes in thickness of its cylindrical wall 2, holes 7 and other singularities, is thus to be tested, in particular the composite material of which it consists.

Figure 2:
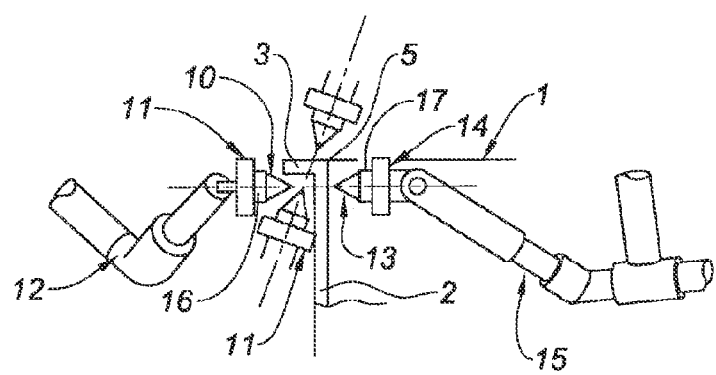
FIG. 2 shows, schematically and in part, an ultrasonic testing installation according to the prior art.
Figure 3:
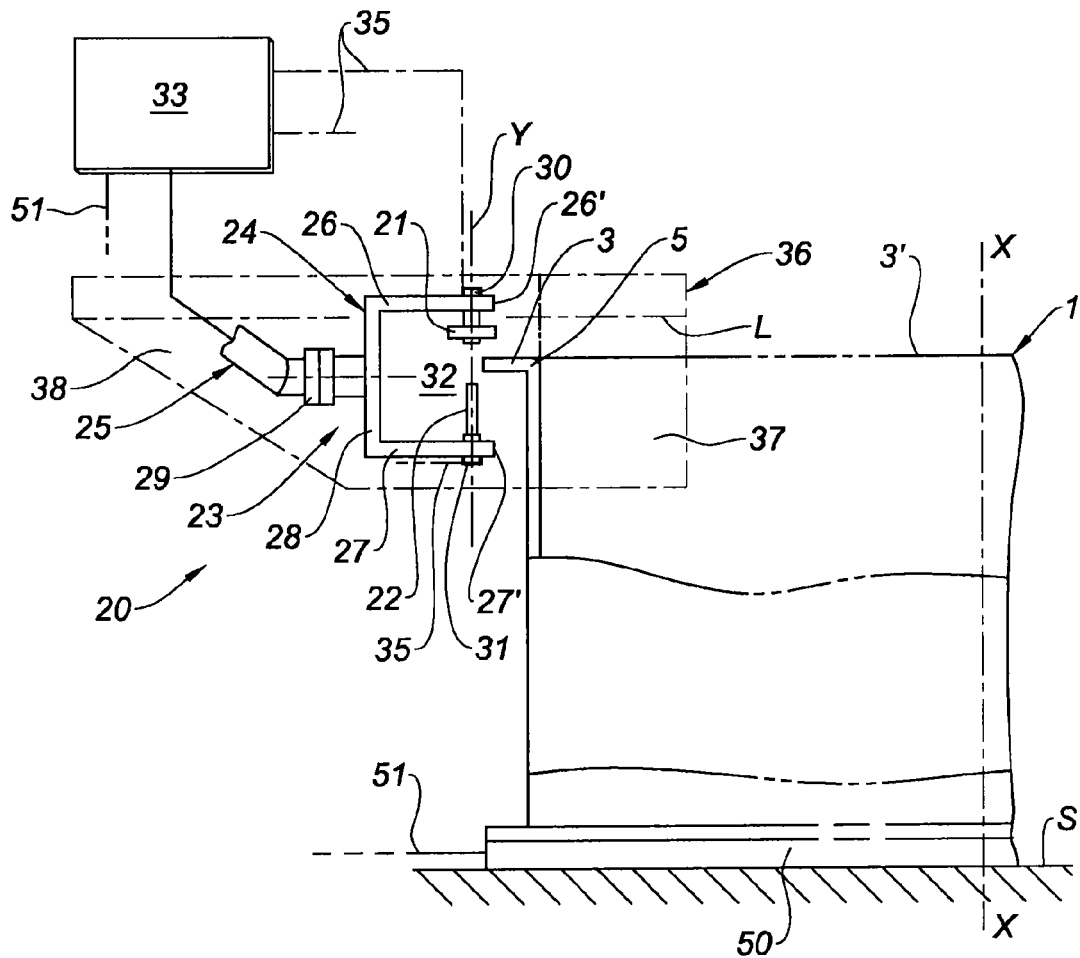
FIG. 3 shows, schematically, an exemplary embodiment of the ultrasonic testing installation according to the invention, intended for testing the flange and connector singularities of said part.

The testing installation 20 according to the invention and as shown in FIG. 3 is of the partial immersion ultrasonic type and is designed, more particularly, to inspect the transverse end flanges 3, 4 and the connecting regions 5, 6 which connect these with the principal region or cylindrical wall 2 of the casing 1. To that end, the installation comprises, principally, two ultrasound transducers, respectively one emitter transducer 21 and one receiver transducer 22 and, advantageously, a common support structure 23 in the form of a stirrup 24 bearing the two transducers 21, 22 and articulated at the end of a moveable control arm 25, for example a robotic arm such as those shown in the embodiment of FIG. 2.

Figure 4:
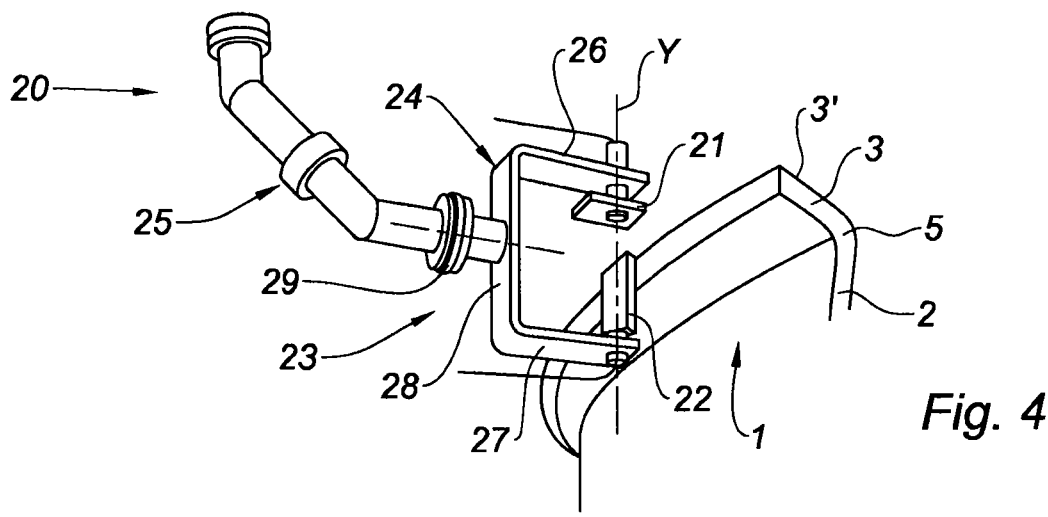
FIG. 4 shows, as a partial perspective, the stirrup shaped structure and the associated transducers of the installation of FIG. 3, ready to test the flange in question of the part.

More particularly, as shown in FIGS. 3 and 4, the stirrup 24 shaped structure 23 is in the shape of a U (or a C or similar) having two opposing lateral branches 26 and 27 (these being parallel in the case of a U shape) and a base (or end) 28 from which the branches project and which is connected, at the other end from the branches, to the moveable arm 25 by means of an articulation (either cylindrical or spherical) 29. The emitter transducer 21 is attached to one branch 26, by means of a screwed-connection member (a bolt or other means) 30 and, conversely, the receiver transducer 22 is attached to the other branch 27, also by means of a screwed-connection member 31. The attachments are such that the transducers 21, 22, once in place, are aligned with respect to one another along one and the same axis Y, which is perpendicular to the branches, for optimum measurement. The transducers 21, 22 are furthermore located close to the free ends 26', 27' of the branches 26, 27 such as to create a maximum inner space 32 in the stirrup 24, between the transducers 21, 22 and the base 28 of the stirrup, so as to engage in its entirety the transverse flange to be tested. The separation between the two transducers is also defined beforehand depending, in particular, on the thickness of the flanges, in order to achieve high quality testing (focusing of the transducers).

FIG. 3 shows, in part, the moveable robotic arm 25 of the installation 20 which permits usual translations and rotations within a three dimensional frame of reference in order to present to the best possible effect the stirrup 24 with its transducers with respect to the singularities to be tested, such as the flange 3 and the connecting region 5 in this example. In this figure, a rectangle 33 represents the control panel for entering and programming the various movements of the arm 25 and of the structure 23, in order to follow to the best possible extent the profile of the transverse flange and of the associated connecting region, as well as the operation and settings of the transducers 21, 22 connected by connections 35 to this panel 33. Other installation controls can also be found on this panel, as will be explained later.

Moreover, by virtue of the fact that a single support structure 23 in the form of a stirrup 24 bears both the emitter transducer 21 and the receiver transducer 22, it is necessary for the testing installation 20 to immerse the region to be tested (flange and connector) only around the stirrup 24 which bears the transducers, in order to facilitate the propagation of the ultrasound waves.

Figure 5:
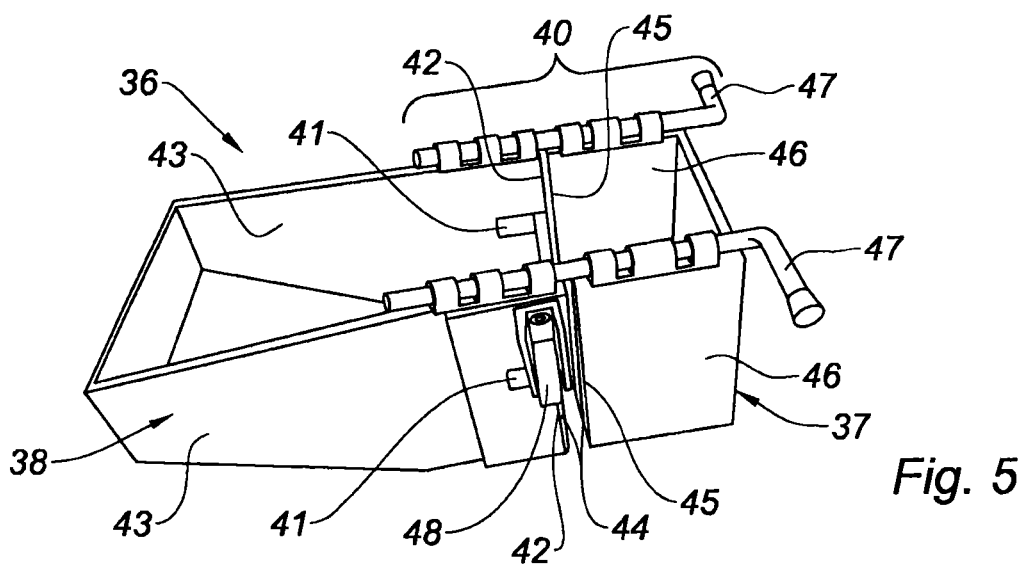
FIG. 5 shows, in perspective, an exemplary embodiment of the immersion container of the installation which provides for immersion of only that region of the part which is being considered by the transducers.
Figure 6:
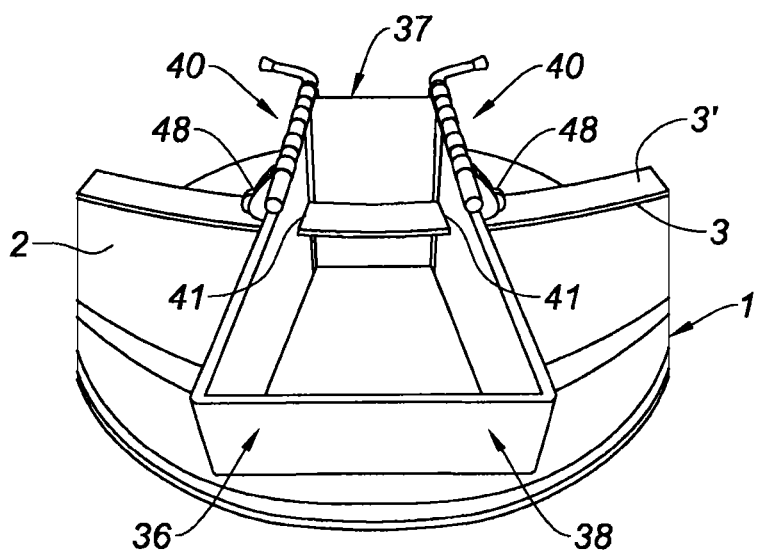
FIG. 6 shows the immersion container of the installation, mounted so as to be immobile on the part to be tested which is moveable.

To that end, as is shown in FIGS. 3, 5 and 6, an immersion container (or tub) 36 (in chain line in FIG. 3) is positioned on the flange in question 3 of the casing 1, straddling this flange, so as to partially immerse, using an appropriate liquid L (water) contained therein, the stirrup 24 shaped structure 23 with its transducers. This container 36 is obtained from a sheet or plate which has been cut and folded as required and has, in the embodiment shown, a roughly parallelepipedal shape which is open on the top side but could have a completely different shape as long as the stirrup 24 shaped structure 23 is housed therein, at the level of the transducers.

In particular, the container 36 consists of two main portions 37 and 38, of which one 37 is located on the inner side of the cylindrical wall 2 of the casing 1, and the other 38 on the outer side. These two portions 37, 38 are joined together so as to prolong one another by a closing means 40 so as to fit together around the flange 3 and the connecting region 5 as far as the cylindrical wall 2. In order to permit this, the outer portion 38 has cutouts 41 which are created in the edge 42 of its respective lateral flanks 43 and which are complementary in shape to the transverse flange 3, such that the latter can engage and fit in the cutouts.

In order to ensure sealing between the container 36 and the casing 1, and to ensure that no liquid leaks from the former, seals 44, for example made of foam, are applied to the edge 42 of the outer portion 38 and to the corresponding edge 45 of the lateral flanks 46 of the inner portion 37 of the container 36. Thus, once the flange 3 has been engaged in the cutouts 41 and the portions of the container have been brought together using the closing means 40, which in this example is of the type having levers 47, the seals 44 press on either side of the cylindrical wall 2 and provide the desired sealing.

Furthermore, the immersion container 36 also rests against the end face 3' of the transverse flange 3 via rolling members 48 such as rollers or casters which are mounted respectively on the longitudinal flanks 43 of the outer portion 38. Moreover, although not shown, rolling members are provided on the inner portion 37 of the container in order to engage with the inner face of the cylindrical wall 2 of the casing.

By virtue of its axisymmetric shape, the casing 1 of the installation 20 shown with reference to FIG. 3 is mounted such that it can move whereas the immersion container 36 is immobile, wherein the rollers 48 roll on the face 3' of the flange while the casing 1 rotates. To that end, the casing is placed on a horizontal rotating plate, represented schematically with the label 50 in FIG. 3 and resting on a support or on the ground S, such that the longitudinal axis of symmetry X is vertical. The transverse flange 4 rests on the rotating plate 50 whereas the opposing transverse flange 3 receives the container 36. The foam seals 44 do not damage the casing, and neither do the rollers—made of rubber or similar—which further hold the container 36 in place on the flanged end of the casing 1 as the casing rotates in order to bring a new sector of the flange to be inspected within the scope of the transducers.

Testing per se of the transverse flange and the associated connecting region by the ultrasonic and partial immersion technique, in order to identify the aforementioned defects therein, is carried out in a conventional manner and will not be discussed in more detail here. Only the operation is described with reference to FIGS. 3, 7 and 8.

Thus, once in particular the container 36 has been placed on the casing 1 and has been filled with water, and the separation of the transducers has been adjusted by the members 30, 31, robotic arm 25 which is programmed for this purpose introduces the structure 23 into the container, such that the stirrup 24 faces the flange 3 as shown in FIG. 3. A preprogrammed horizontal movement (radial with respect to the axis X of the casing) of the arm 25 causes the two transducers 21, 22 to pass respectively either side of the flange 3 which is immersed in the liquid L, with the axis Y of these transducers perpendicular to the flange, which engages progressively, between them, into the internal space 32 of the stirrup.

Figure 7:
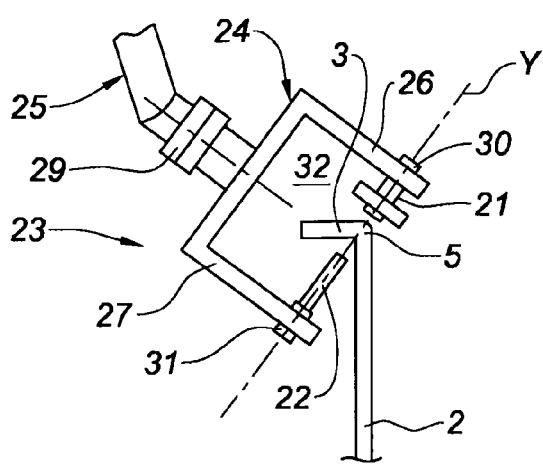
FIGS. 7 and 8 show, schematically, phases of the operation of the stirrup shaped structure of the installation for inspecting the flange in question of said part.
Figure 8:
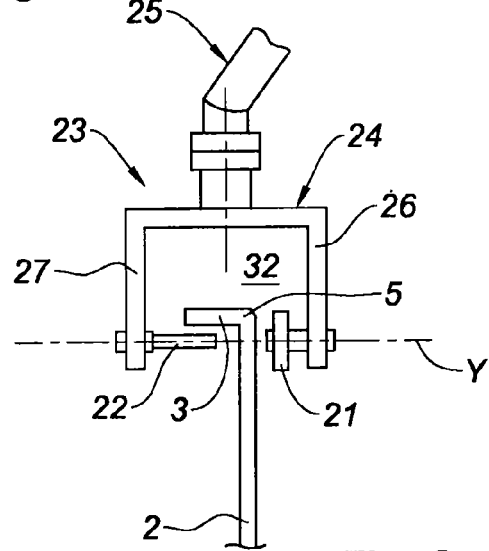

The flange 3, the profile of which is flat, is thus tested, and when the stirrup arrives at the connecting region 5, the robotic arm 25, which is articulated to the structure 23, causes the stirrup to pivot progressively in order to follow the profile encountered, as shown in FIG. 7. The space 32 is such that it allows the flange to engage without touching the stirrup. The stirrup 24 continues to pivot in this way until the transducers 21 and 22 reach the cylindrical wall 2, the axis Y still being perpendicular to the wall encountered for optimum testing, as shown in FIG. 8. The U shape of the stirrup thus makes it possible to follow the profile of the flange 3 and the connecting region 5 as far as the wall 2, the internal space 32 of the stirrup serving to receive the flange and the connector without touching them.

Once this sector of the flange has been tested in order to identify any aforementioned defects therein, the stirrup 24 shaped structure 23 is withdrawn from the flange 3 by a reverse movement of the arm 25 and, via the rotating plate 50 connected by the connection 51 to the control panel 33 and driving the casing 1 in rotation, a subsequent sector of the flange 3 is brought into the immobile immersion container for analysis.

In this case testing of the flange proceeds stepwise, but it is also conceivable to conduct continuous testing of the flange, without stopping the rotating plate.

Figure 9:
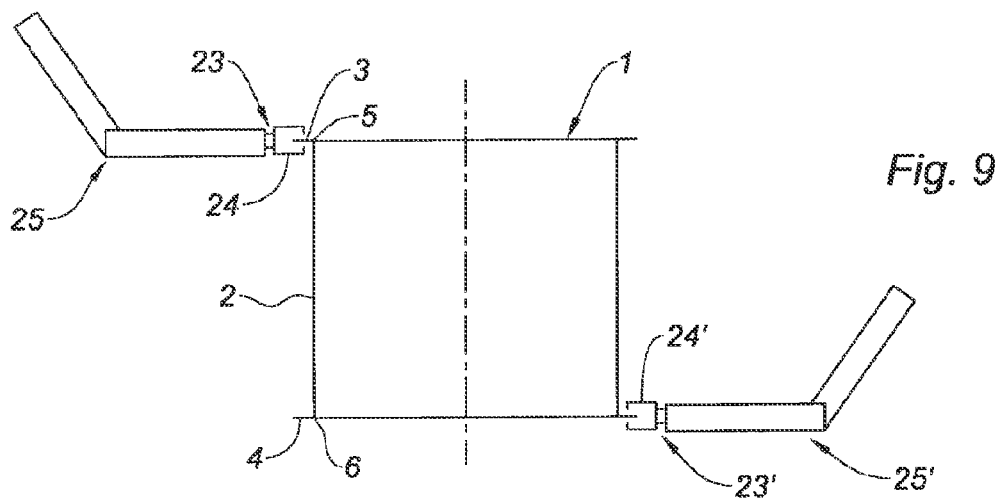
FIG. 9 shows, schematically, two stirrup shaped structures of the installation for respectively inspecting, simultaneously, the two transverse end flanges of the axisymmetric part.

As shown highly schematically in FIG. 9, testing of both transverse end flanges—respectively the upper flange 3 and the lower flange 4—of the casing 1 can be conducted concomitantly using two robotic arms 25 and 25' such as those 12, 15 of the preceding installation 9. The latter is used before or after testing of the flanges for testing the cylindrical wall 2 using the supports 11, 14 of the transducers 10, 13. The two stirrup 24, 24' support structures 23, 23' having the transducers are mounted at the end of the respective arms and each of these is housed in the immersion container provided on each flange (and not represented in this figure). Of course, the lower flange does not rest on the rotating plate and the casing is driven in rotation by another means. Thus, using one and the same installation, the entire profile of the casing 1 and thus the composite material is tested perfectly, simply by changing the transducer support structures at the ends of the robotic arms.

The advantages of the solution having a support structure in the form of a stirrup bearing both transducers and the associated immersion container are in particular: being able to approach and access the flange regions and connecting regions of the casing without difficulty by virtue of the stirrup shape; ensuring effective and lower cost coupling (a simple folded and cutout container); using one or both of the robotic arms of the initial installation in order to test the flanges either successively or simultaneously; avoiding testing with the flanged casing being entirely immersed; easily following the profile of the flanges by the tolerance left by the stirrup; mounting the stirrup shaped structure onto the arms and removing it therefrom simply and quickly, and doing the same for the container on the casing without damaging the latter; and testing the flanges and connecting regions quickly and reliably, thus improving the quality of the ultrasonic testing.

The invention claimed is:

1. An installation for an ultrasonic immersion testing of a tubular part including a cylindrical wall terminated by a transverse end flange projecting from the cylindrical wall via a connecting region having an inner radius on a flange side which is smaller than an outer radius opposed thereto, the installation comprising:
   emitter and receiver transducers in contact with a coupling liquid for emitting and for receiving ultrasounds, respectively, and configured to be arranged and aligned respectively on either side of the flange to be tested;
   a structure in a form of a U shaped or C shaped stirrup, wherein ends of opposing branches of the stirrup respectively bear the emitter transducer and the receiver transducer aligned with respect to each other along an axis perpendicular to the branches so as to present an internal space through which the flange to be tested can pass without touching the stirrup, and wherein a base is mounted in an articulated manner at an end of a moveable control arm; and
   an immersion container inside which is arranged the stirrup shaped structure bearing the emitter and receiver transducers and which includes a liquid for coupling the emitter and receiver transducers to one another, wherein the container is shaped to be arranged over the flange to be tested and includes first and second portions configured to engage and straddle, with sealing, the transverse flange and the cylindrical wall of the tubular part.

2. The installation as claimed in claim 1, wherein the emitter and receiver transducers are adjustably mounted to the respective opposing branches so as to adjust separation between the emitter and receiver transducers.

3. The installation as claimed in claim 1, wherein the immersion container straddles the flange with sealing as far as the cylindrical wall and can be moved relative to the tubular part to test an entire periphery of the flange.

4. The installation as claimed in claim 1, wherein the immersion container is immobile with respect to the tubular part which can be rotated about a longitudinal axis of symmetry of the tubular part, the immersion container including rolling members configured to engage with a transverse outer face of the flange.

5. The installation as claimed in claim 1, wherein the first and second portions of the immersion container are joined together using a closing mechanism, the first portion including cutouts for engaging the transverse flange and for straddling, with the second portion, the flange as far as the cylindrical wall of the tubular part, seals being provided between the joined together portions and the tubular part.

6. The installation as claimed in claim 4, wherein a rotating plate rotates the tubular part.

7. The installation as claimed in claim 1, wherein two structures in a form of stirrups including emitter transducers and receiver transducers and respective controllable arms are provided to be able to test, simultaneously, two transverse end flanges of the tubular part, the two structures being arranged in respective immersion containers including the liquid for coupling of the emitter and receiver transducers and shaped to be disposed on respective transverse flanges.

8. The installation as claimed in claim 1, wherein the moveable control arm articulates the structure such that the stirrup pivots so as to follow a profile of the flange, the connecting region, and the cylindrical wall, the axis being parallel to the cylindrical wall in a first position of the stirrup, the axis passing through the connecting region in a second position of the stirrup, and the axis being perpendicular to the cylindrical wall and the internal space receiving the flange in a third position of the stirrup.

9. The installation as claimed in claim 5, wherein the closing mechanism includes levers.

* * * * *